(12) United States Patent
Hassler et al.

(10) Patent No.: US 7,182,787 B2
(45) Date of Patent: Feb. 27, 2007

(54) TRAPEZIUM OR TRAPEZOMETACARPAL IMPLANT

(75) Inventors: Michel Hassler, Saint-Ismier (FR); Cecile Real, Grenoble (FR); Jean-Pierre Pequignot, Nice (FR); Yves Allieu, Montpellier (FR)

(73) Assignee: Bioprofile, Grenoble Cedex (FR)

( * ) Notice: Subject to any disclaimer, the term of this patent is extended or adjusted under 35 U.S.C. 154(b) by 0 days.

(21) Appl. No.: 10/498,491

(22) PCT Filed: Dec. 9, 2002

(86) PCT No.: PCT/IB02/05189

§ 371 (c)(1),
(2), (4) Date: Jan. 11, 2005

(87) PCT Pub. No.: WO03/049651

PCT Pub. Date: Jun. 19, 2003

(65) Prior Publication Data

US 2005/0119757 A1    Jun. 2, 2005

(30) Foreign Application Priority Data

Dec. 12, 2001   (FR) ................................ 01 16091

(51) Int. Cl.
*A61F 2/42* (2006.01)
(52) U.S. Cl. .................................................. 623/21.15
(58) Field of Classification Search ............ 623/18.11, 623/21.15, 21.11, 21.16, 21.17, 21.19
See application file for complete search history.

(56) References Cited

U.S. PATENT DOCUMENTS 3,745,590 A    7/1973   Stubstad
3,924,276 A   12/1975   Eaton
5,702,469 A * 12/1997   Whipple et al. .......... 623/21.15
5,728,163 A *  3/1998   Maksene ................... 623/21.15

FOREIGN PATENT DOCUMENTS

| DE | 297 21 522 | 2/1998 |
|----|------------|--------|
| DE | 199 25 529 | 12/2000 |
| FR | 2 680 967 | 3/1993 |

OTHER PUBLICATIONS

Allieu et al., "Swanson Trapezial Implant in the Treatment of Peritrapezial Arthrosis—A study of eight cases", Ann. Chir. Main, vol. 3, No. 2, 1984, pp. 113-123.

* cited by examiner

*Primary Examiner*—Eduardo C. Robert
*Assistant Examiner*—Michael J. Araj
(74) *Attorney, Agent, or Firm*—Young & Thompson

(57) ABSTRACT

The implant includes a stem terminating in a head. The stem is adapted to be inserted in the metacarpus of the thumb and the head to be disposed in a space obtained particularly by removing at least a portion of the trapezium. The surface of the head is constituted by a base connected to the stem and adapted to rest on the proximal end of the metacarpus, a distal surface portion opposite the base and serving as a contact surface with the bone located facing the proximal end of the metacarpus, and a connecting portion connecting the base and the distal surface portion of the head. The distal surface portion of the head is inclined relative to a longitudinal axis of the stem by a predetermined angle, such that, when the stem is mounted straight in the metacarpus, the distal surface portion of the head can be located in varus.

15 Claims, 5 Drawing Sheets

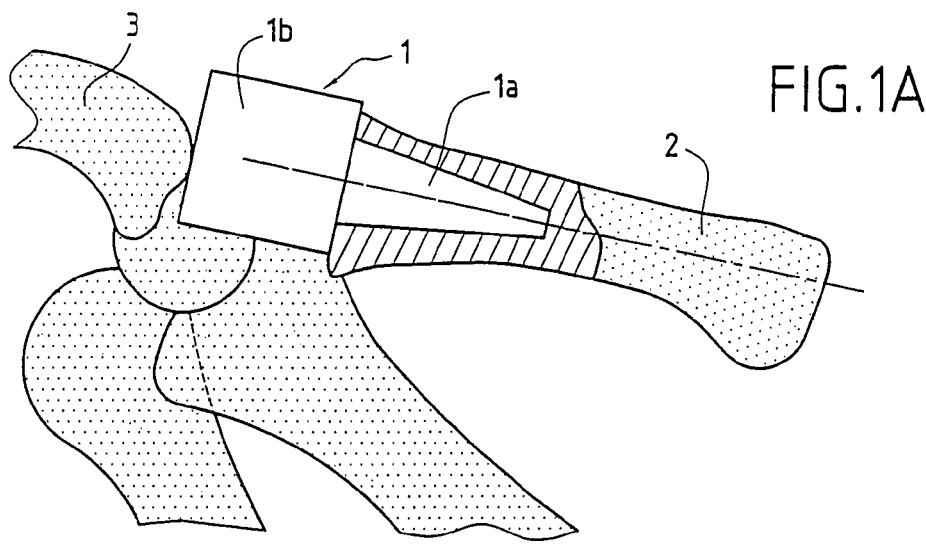
FIG.1A
FIG.1B
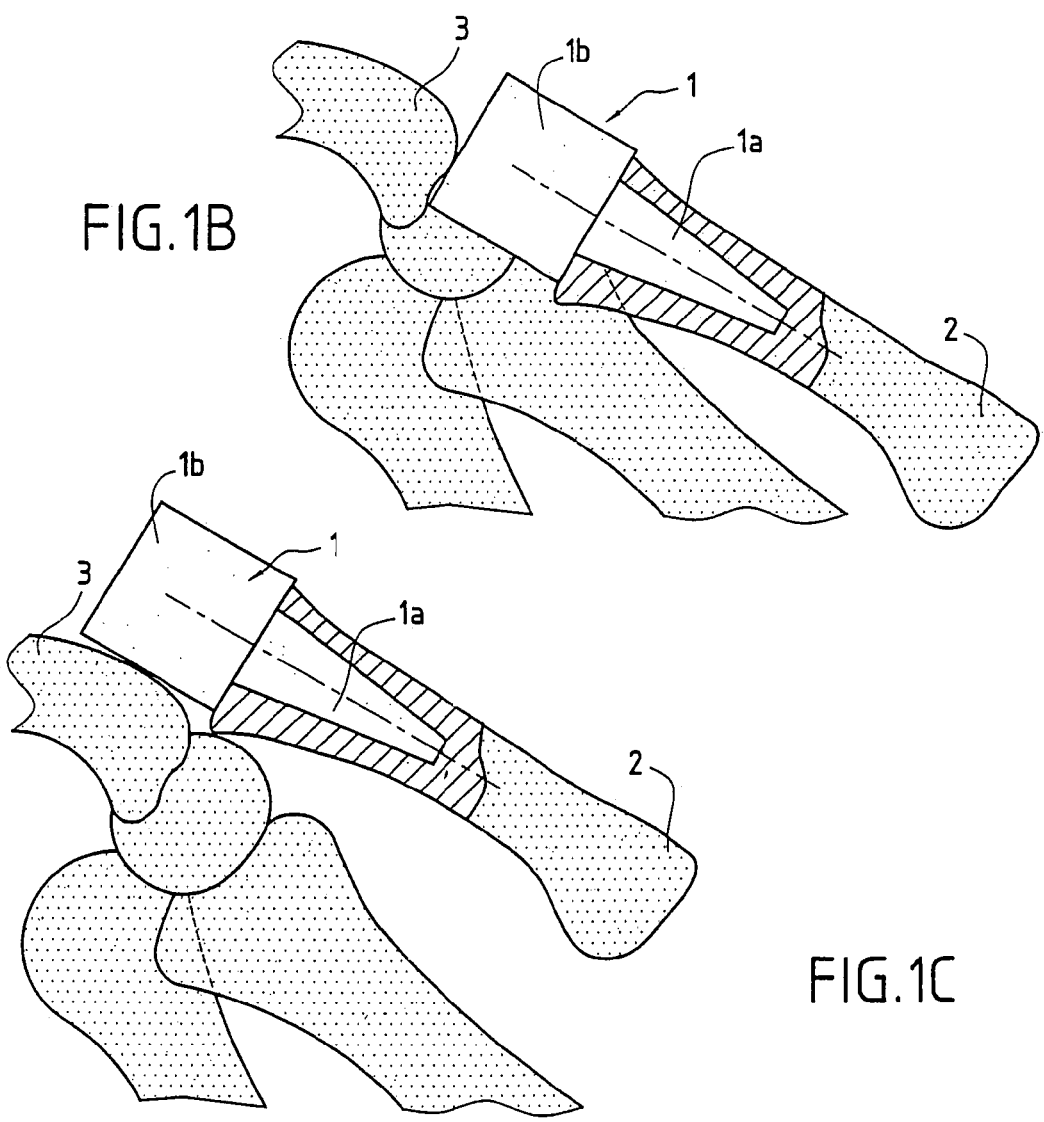
FIG.1C

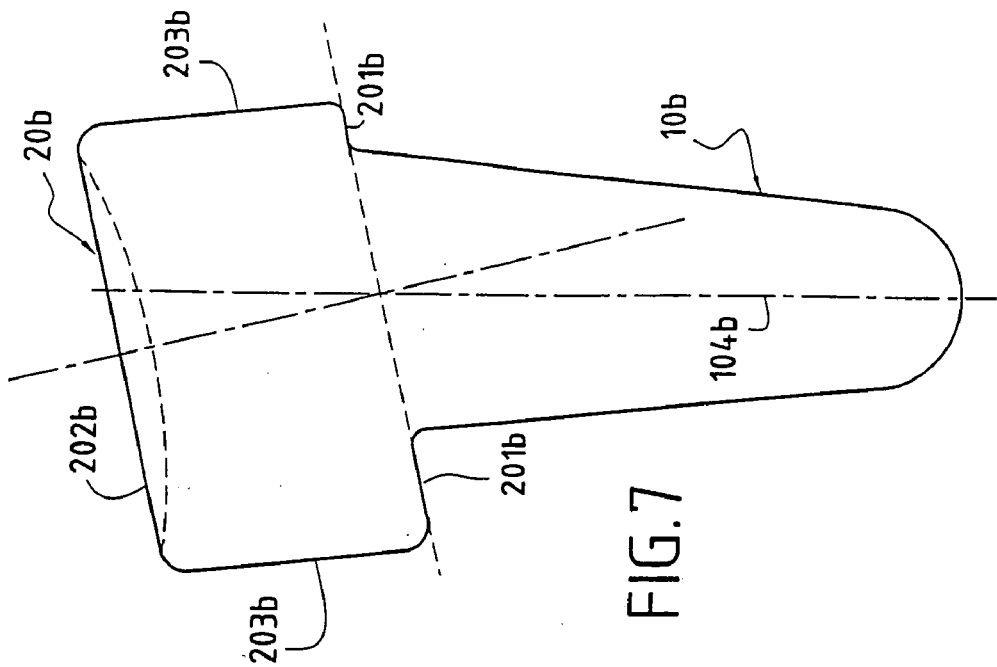
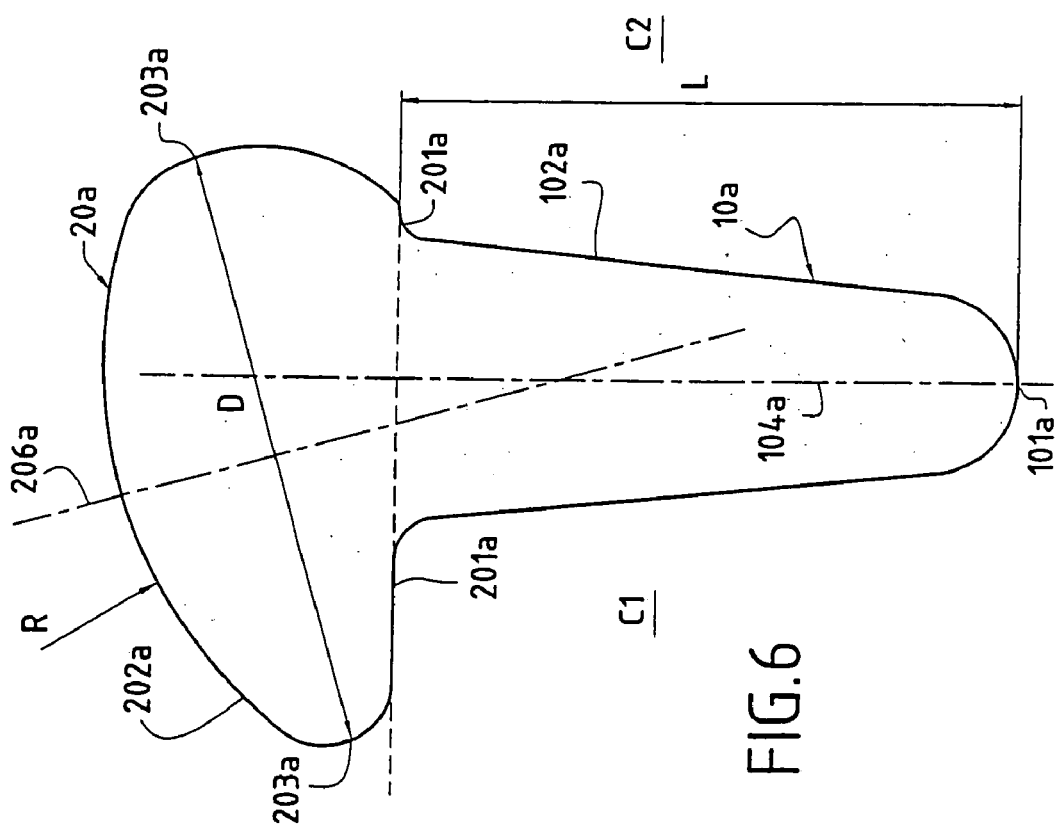

TRAPEZIUM OR TRAPEZOMETACARPAL IMPLANT

FIELD OF THE INVENTION

The present invention relates to a trapezal or a trapezo-metacarpal implant, comprising a stem terminating in a head. The stem is adapted to be inserted in the metacarpus of the thumb, and the head to be disposed in a space obtained particularly by removing all the trapezium, in the case of a trapezal implant, or a portion of the trapezium, in the case of a trapezo-metacarpal implant.

The implant according to the invention can be used to treat rhizarthritis, a very frequent affliction consisting in an arthritis of the base of the thumb, essentially trapezo-metacarpal.

STATE OF THE ART

There exist several types of trapezal and trapezo-metacarpal implants.

Among the most widely known are the so-called Swanson trapezal implant, constituted by a stem terminating in a head, the entirety made of silicone. In this implant, the head has a suitable size and shape to replace all the trapezium.

This implant has two principal drawbacks:
the material from which it is made is unsuitable: silicone gives rise in certain patients to an allergy known as siliconite; moreover, because of its insufficient hardness, the silicone wears in contact with the adjacent bones, giving rise to deterioration of the implant;
it is not stable and, in particular, has a tendency to dislocate, fully or partially; FIGS. 1A, 1B and 1C show a trapezal implant 1, whose stem 1a is mounted in the metacarpus 2 and the head 1b completely replaces the trapezium; in FIG. 1A, the implant is normally positioned relative to the adjacent bones and particularly relative to the scaphoid 3 with which it is in contact; FIG. 1B shows a typical configuration of partial dislocation of the implant during a pinching effort involving the thumb and at least one other finger of the hand; FIG. 1C shows a typical arrangement of full dislocation of the implant after such a pinching effort.

So as to increase the stability of this implant and avoid partial dislocation as shown in FIG. 1B or full dislocation as shown in FIG. 1C, it has been proposed to perforate its head from one side to the other so as to pass therethrough a tendinous tongue adapted to limit its movements, or to ligate it. These techniques complicate the task of the surgeon and limit the mobility of the implant, causing trouble for the patient.

Another solution is described in the article entitled "L'implant trapézien de Swanson dans le traitement de l'arthrose péri-trapézienne" ("The Swanson trapezal implant in the treatment of peri-trapezal arthritis"), by Y. Allieu et al., which appeared in the review "Annales de Chirurgie de la Main" ("Annals of Surgery of the Hand"), Volume 3, No. 2, 1984. It consists in first carrying out an oblique cut at the proximal end of the metacarpus, and fixing the implant in the varus position, which is to say fixing it in an inclined manner relative to the axis of the metacarpus by orienting it inwardly of the hand, as shown in FIG. 2. Thus inclined, the implant is held in contact with the scaphoid, and has less tendency to dislocate. This solution thus significantly improves the stability of the implant. Nevertheless, fixing the implant in an inclined manner relative to the axis of the metacarpus requires providing an oblique hole in the shaft of the metacarpus, a delicate surgical operation to perform, which requires hollowing out the hard peripheral portion of the bone and which moreover renders this latter fragile.

There are also known trapezo-metacarpal implants, such as the Swanson condylar implant, whose head is to be disposed in the space provided on the one hand by forming a cut on the proximal end of the metacarpus and on the other hand by removing a portion of the trapezium opposite this proximal end. These implants are also made of silicone. A titanium version of the Swanson condylar implant however has been proposed.

In the same way as for the Swanson trapezal impant, the material from which these trapezo-metacarpal implants are made is unsuitable. As previously explained, silicone is too soft. As for titanium, it is too hard and wears the bones with which it is in contact. It also makes the implant painful for the patient.

Moreover, these implants have a relatively thick and narrow head, adapted to be disposed in a cavity of matching shape previously formed in the trapezium. This co-action between a thick and narrow head and a deep and narrow cavity gives stability to the implant—which is the intended purpose—because the head is retained in the cavity, but does not take account of the anatomical curvature of the trapezo-metacarpal articulation, which is suitable for ample relative movements between the trapezium and the proximal end of the metacarpus. By way of illustration, FIG. 3 shows the Swanson condylar implant with its stem 5a inserted in the metacarpus 2 of the thumb and its head 5b disposed in a deep and narrow cavity in the trapezium 6. The small radius of curvature of the surface portion of the head in contact with the trapezium, made necessary by the thickness and narrowness of the head, limits the angular swing of the implant, which hinders movements of the thumb.

OBJECTS AND SUMMARY OF THE INVENTION

The present invention seeks particularly to provide a trapezal or a trapezo-metacarpal implant which will be at least as stable as the implants described above and which will be relatively easy to emplace.

To this end, there is provided a trapezal or trapezo-metacarpal implant comprising a stem terminating in a head, the stem and the head being adapted respectively to be inserted in the metacarpus of the thumb and to be disposed in a space obtained particularly by removing at least a portion of the trapezium, the surface of the head being constituted by a base connected to the stem and adapted to rest on the proximal end of the metacarpus, a distal surface portion opposite the base and serving as a contact surface with the bone located facing the proximal end of the metacarpus, and a connection portion connecting the base and the distal surface portion of the head, characterized in that the distal surface portion of the head is inclined relative to a longitudinal axis of the stem by a predetermined angle, such that, when the head is mounted straight in the metacarpus, the distal surface portion of the head can be located in varus. Said bone facing the proximal end of the metacarpus is the scaphoid in the case of a trapezal implant, and the remaining portion of the trapezium in the case of a trapezo-metacarpal implant.

Thus, according to the invention, the stability of the implant is given by the varus position of the distal surface portion of the head, as in the mentioned article by Y. Allieu et al. "L'implant trapézien de Swanson dans le traitement de l'arthrose péri-trapézienne" ("The Swanson trapezal implant in the treatment of peri-trapezal arthritis"). However, unlike this article, it is not the entire implant which is positioned in varus, but only a portion of the implant, including the distal surface portion of the head.

The inclination of the distal surface portion of the head relative to the stem permits inserting the stem straight into the metacarpus, which is to say along the longitudinal axis of this latter. The stem can thus be placed exclusively in the soft central portion of the bone, which facilitates the work of the surgeon who does not have to cut into the hard peripheral portion. Such a positioning of the stem moreover avoids rendering the bone excessively fragile.

There is no need, according to the invention, to ligate the implant or to pass a tendon through it. On the other hand, contrary to the trapezo-metacarpal implants of the prior art, the head can be wide and its distal surface portion can have a large radius of curvature corresponding substantially to the radius of curvature of the trapezo-metacarpal articulation. The head can also be flatter. The surgeon thus does not need to make a large cut on the proximal end of the metacarpus, nor to cut deeply into the trapezium, for which the removal of a small cap of large radius of curvature can suffice.

The stability of the implant according to the invention can be further increased by designing this latter such that the distal surface portion of the head will be not only inclined but also offset relative to the longitudinal axis of the stem to the side of the implant where the angle between the distal surface portion of the head and the longitudinal axis of the stem is smaller.

Preferably, at least the distal surface portion of the head is made of pyrocarbon. Pyrocarbon has a very good coefficient of friction with bone, which permits it to slide without adherence over the bones with which it is in contact and without giving rise to wear. In contrast to silicone, which is too soft, and titanium, which is too hard, pyrocarbon has a modulus of elasticity, also called Young's modulus, near that of bone. The reciprocal forces exerted on the implant and the neighboring bones thus distribute themselves evenly, thus reducing the risk of pain for the patient.

BRIEF DESCRIPTION OF THE DRAWINGS

In the accompanying drawings:

FIGS. 1A, 1B and 1C, already discussed, show a portion of a hand in which has been implanted a trapezal implant according to the prior art, respectively in the rest position, in pinching position with the implant partially dislocated, and in pinching position with the implant fully dislocated, this portion of the hand being seen on the dorsal side, with the thumb and trapezo-metacarpal articulation in profile and the other fingers seen from above;

FIG. 6 shows in profile view a trapezo-metacarpal implant according to a second embodiment of the invention;

FIG. 7 shows in profile view a trapezal implant according to a third embodiment of the invention.

DETAILED DESCRIPTION OF SEVERAL EMBODIMENTS OF THE INVENTION

Figure 2:
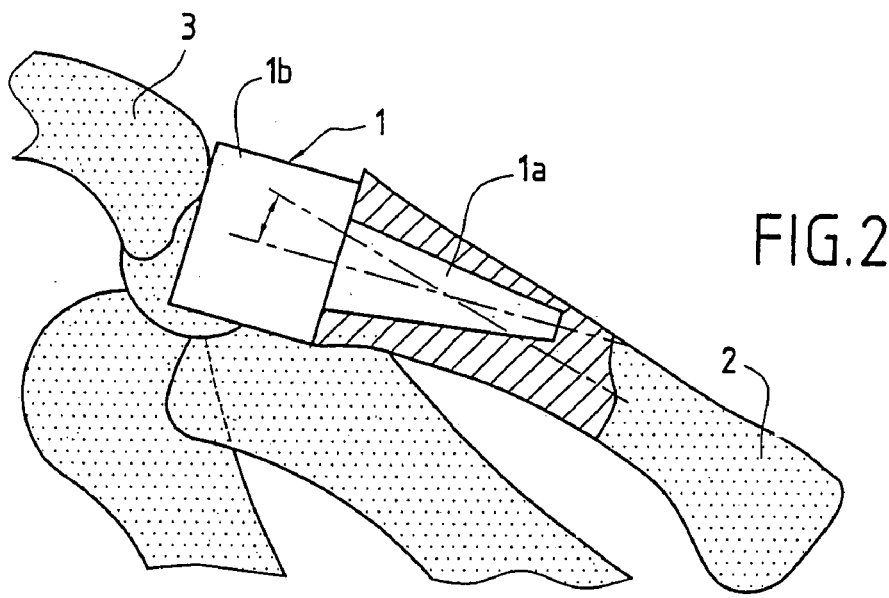
FIG. 2, already discussed, shows, in the same type of view as that of FIGS. 1A, 1B and 1C, a trapezal implant according to the prior art mounted obliquely in the metacarpus of the thumb.
Figure 3:
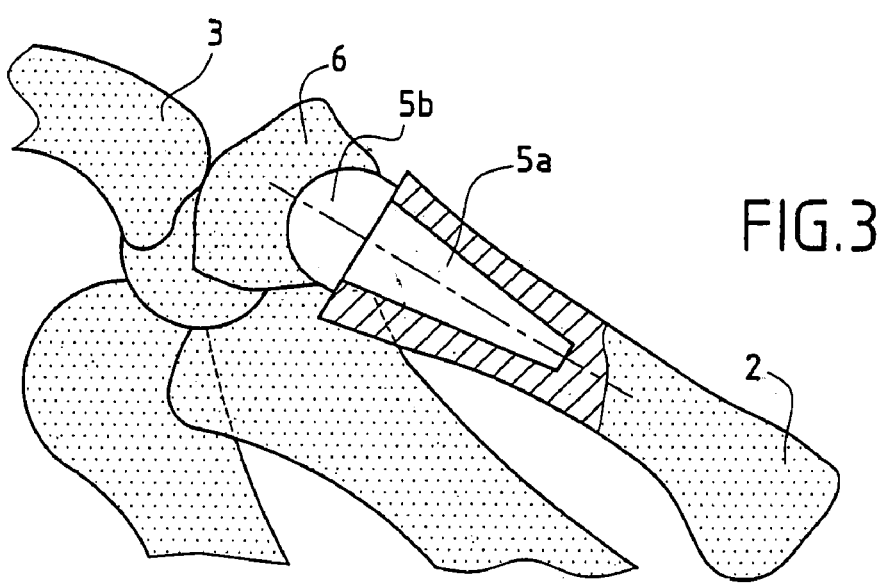
FIG. 3, already discussed, shows, in the same type of view as that of FIGS. 1A, 1B and 1C, a trapezo-metacarpal implant according to the prior art mounted in the metacarpus of the thumb.
Figure 4A:
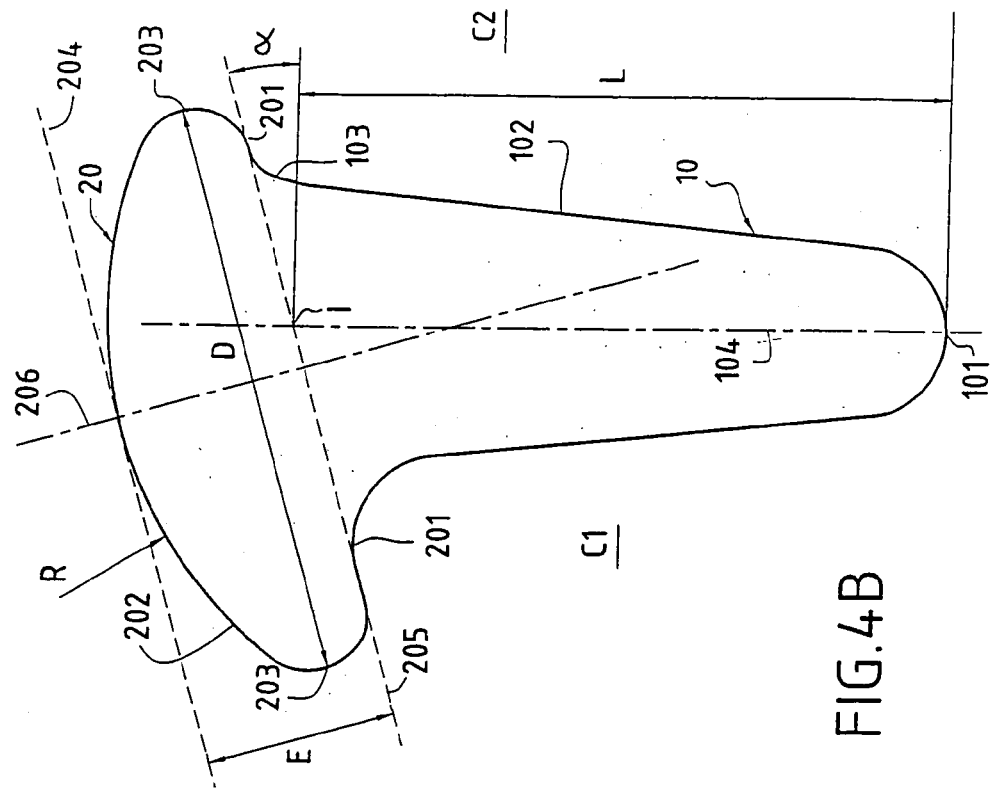
FIG. 4A shows in profile view a trapezo-metacarpal implant according to a first embodiment of the invention.

FIG. 4A shows an implant according to a first embodiment of the invention.

The implant according to this first embodiment is a trapezo-metacarpal implant, in the general form of a nail. It comprises a stem 10 terminating, at a so-called proximal end, in a head 20 and whose opposite end, called the distal end, is constituted by a point 101.

Stem 10 is adapted to be inserted in the metacarpus of the thumb, and the head 20 to be disposed in a space obtained on the one hand by providing a cut or resection on the proximal end of the metacarpus and on the other hand by removing a portion of the trapezium facing the proximal portion of the metacarpus.

The head 20 has a flattened shape. Its longitudinal section is circular. Its surface is constituted by an annular and plane base 201 connected to the proximal end of the stem 10 and adapted to rest on the proximal portion of the metacarpus, a distal surface portion 202 opposite the base 201 and serving as a contact and friction surface with the remaining portion of the trapezium, and a rounded and annular lateral edge 203 connecting the distal surface portion 202 to the base 201. Among the surface portions 201, 202 and 203, only the distal portion 202 is liable to be in contact with the remaining portion of the trapezium. The distal surface portion 202 has a convex shape, and preferably consists in a spherical cap.

The stem 10 comprises a truncated conical portion 102 whose smaller diameter end is connected to the point 101 and larger diameter end is prolonged by a divergent connecting portion 103 connecting the base 201 of the head 20 to the truncated conical portion 102 of the stem 10.

According to the invention, the distal surface portion 202 of the head 20 is inclined relative to a longitudinal axis 104 of the stem 10 by a predetermined angle $\alpha$, which is to say that the mean plane 204 tangent to the distal surface portion 202 forms with the longitudinal axis 104 of the stem 10 an angle $\beta=90°-\alpha$ different from 9020 . In the embodiment shown in FIG. 4A, the head 20 in its totality is inclined relative to the axis 104 of the stem 10. Thus, in particular, the base 201 is inclined relative to the axis 104 in the same direction as the distal surface portion 202, and by the angle $\alpha$. The angle of inclination $\alpha$ is typically at least equal to 10° and preferably equal to 15°.

The diameter D of the head 20 and the radius of curvature R of the distal surface portion 202 are selected to be sufficiently great to match as much as possible the anatomical curvature of the trapezo-metacarpal articulation. Typically, the implant according to the invention is designed in four different sizes. In each of these sizes, the ratio between the diameter D of the head, measured along a longitudinal axis of the head inclined relative to the longitudinal axis 104 of the stem in the same direction as the distal surface portion 202 and by an angle equal to the angle $\alpha$, and the length L of the stem, measured along the longitudinal axis 104 of the stem between the distal end 101 and the point of intersection I between the plane 205 defined by the base 201 and the axis 104, is preferably equal to at least 0.84. The ratio between the radius of curvature R of the distal surface portion 202 and the length L of the stem is preferably equal at least to 0.6.

The thickness E of the head can be relatively small. Typically, the ratio between the thickness E of the head 20, measured perpendicularly to the base 201, and the length L of the stem, is at most equal to 0.42.

Preferably, the distal surface portion 202 of the head 20 is not only inclined, but also offset relative to the longitudinal axis 104 of the stem 10 to the side of the implant where the angle between the distal surface portion 202 and the axis 104 is smaller, which is to say the side designated in FIG. 4A by the reference C1 and corresponding to the angle β=90°−α. In this first embodiment, all of the head 20 is offset relative to the axis 104 to the side C1. Thus, the geometric center of the head 20, like the center of the distal surface portion 202, is located beyond the axis 104, on the side C1.

Figure 4B:
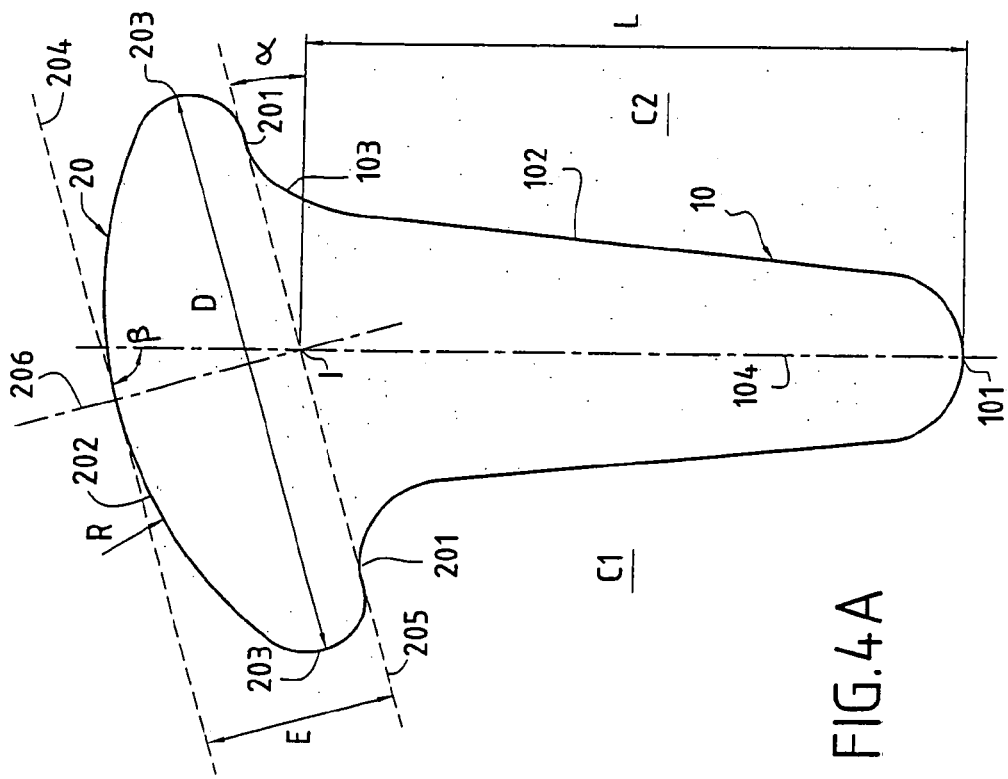
FIG. 4B shows in profile view a modification of the implant according to the first embodiment of the invention.

In the example shown in FIG. 4A, in which the distal surface portion 202 has a spherical shape, the axis of symmetry 206 of the distal surface portion 202 intersects the longitudinal axis 104 of the stem 10 at the point I of intersection between the plane 205 defined by the base 201 of the head 20 and the axis 104. However, as a modification, the distal surface portion 202 could be further offset relative to the stem 10. FIG. 4B shows such an arrangement, in which the axis of symmetry 206 of the distal surface portion 202 intersects the longitudinal axis 104 of the stem 10 at a point located between the distal end 101 of the stem 10 and the point I of intersection between the plane 205 defined by the base 201 and the axis 104.

The implant according to the invention, constituted by the stem 10 and the head 20, or at least the distal surface portion 202 of the head 20, is preferably made of pyrocarbon. According to a preferred variant, the implant is constituted by a graphite substrate clad with a layer of pyrocarbon.

Figure 5:
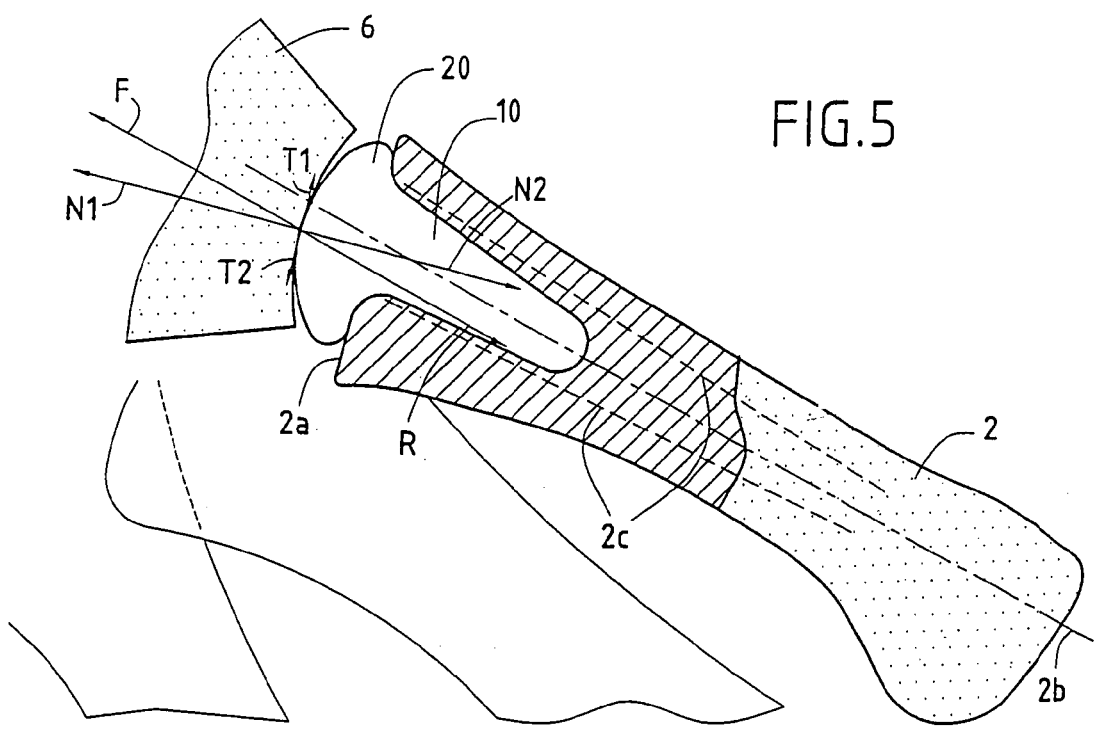
FIG. 5 shows, in the same type of view as those of FIGS. 1A, 1B and 1C, the implant according to the first embodiment of the invention emplaced in the hand of a patient.

Referring to FIG. 5, the implant according to the invention is emplaced in the following manner:

An oblique varus cut is provided in the proximal end 2a of the metacarpus 2 and a portion of the trapezium 6 located facing this proximal end 2a is removed, to provide a space adapted to accommodate the head 20. Then a straight hole is formed in the shaft of the metacarpus, along the longitudinal axis 2b of this latter. The stem 10 of the implant is then force-fitted into the hole until the inclined base 201 of the head 20 comes into contact with the inclined surface 2a of the metacarpus, such that the head 20 will be disposed in the mentioned space, in a varus position.

The stem 10 of the implant is thus positioned straight in the central soft portion of the metacarpus, delimited in FIG. 5 by broken lines 2c, and is surrounded by the hard peripheral portion of this latter. The emplacement of the implant is thus not more complicated than for the Swanson trapezal implant shown in FIGS. 1A, 1B and 1C. Moreover, once emplaced as described above, the implant is more stable than the Swanson trapezal implant. This stablity of the implant according to the invention is due principally to the fact that the surface of the implant in contact with the trapezium is increased by the varus position of the distal surface portion 202. FIG. 5 shows the balance of forces exerted between the implant according to the invention and the trapezium when the patient exerts a pinching effort by securely holding an object between the thumb and index finger. In this arrangement, the implant exerts on the trapezium a force F having a component T1 tangential to the contact surface and a component N1 perpendicular to this contact surface. The large contact surface between the trapezium and the head of the implant permits the trapezium to exert in response, a reaction force R having a tangential component T2 sufficiently great to counterbalance the tangential component T1 of the force F. This balancing of forces holds the implant in contact with the trapezium and thus significantly reduces the risk of dislocation.

FIG. 6 shows a second embodiment of the implant according to the invention. The implant according to this second embodiment is a trapezo-metacarpal implant which differs from the implant according to the first embodiment essentially in that only the distal surface portion 202a is inclined relative to the stem 10a, and not the entire head 20a. Thus, the base 201a of the head 20a is perpendicular to the longitudinal axis 104a of the stem 10a. The connection portion 203a of the head 20a is thus higher on the side C2 of the implant where the angle between the distal surface portion 202a and the axis 104a is greater, than on the opposite side C1.

As in the first embodiment, the distal surface portion 202a is preferably offset relative to the axis 104a of the stem to the side C1.

The ratios indicated above between the diameter D of the head and the length L of the stem, and between the radius of curvature R of the distal surface portion of the head and the length L of the stem, also hold true for this second embodiment. On the other hand, the thickness of the head is necessarily greater.

When it is emplaced in the patient, this implant rests on a straight cut previously provided in the proximal end of the metacarpus, and not on an oblique cut as in the first embodiment.

FIG. 7 shows a third embodiment of the invention. The implant according to this third embodiment is a trapezal implant, which is to say that the head 20b has a shape and size suitable to replace all the trapezium. The distal surface portion 202b of the implant has a concave shape which permits it to co-act with the distal portion of the scaphoid. The head 20b, including the base 201b, the distal surface portion 202b and the connecting portion 203b, is inclined similarly to the first embodiment.

Figure 8:
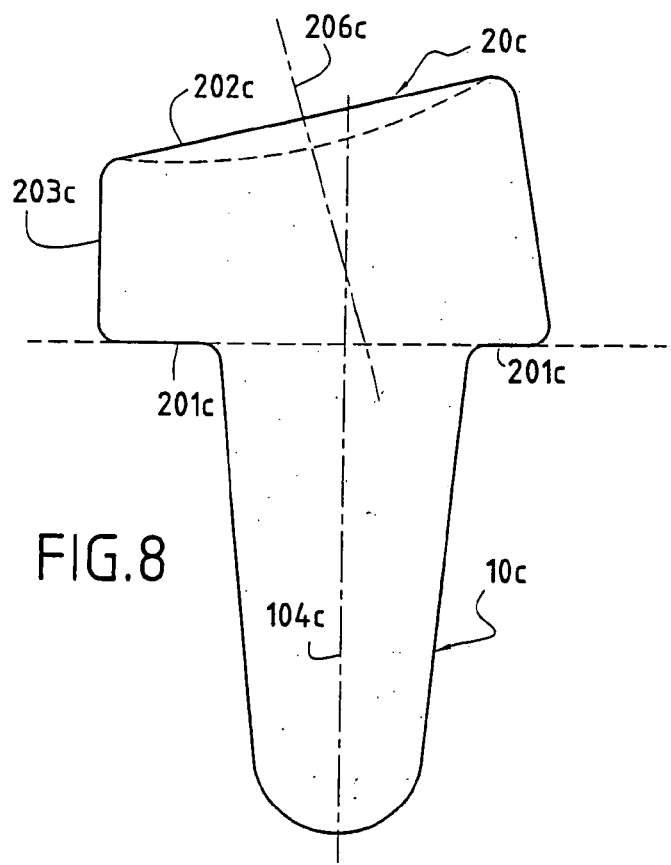
FIG. 8 shows in profile view a trapezal implant according to a fourth embodiment of the invention.

FIG. 8 shows a fourth embodiment of the invention. The implant according to this fourth embodiment is a trapezal implant whose head 20c comprises a distal surface portion 202c inclined relative to the axis 104c of the stem 10c and a base 201c perpendicular to the axis 104c. As in the second embodiment, this implant is adapted to rest on a straight cut previously provided in the proximal end of the metacarpus.

The invention claimed is:

1. A Trapezal or trapezo-metacarpal implant comprising a stem terminating in a head, the stem and the head being adapted respectively to be inserted in the metacarpus of the thumb and to be disposed in a space obtained particularly by removing at least a portion of the trapezium, the surface of the head being constituted by a base connected to the stem and adapted to rest on the proximal end of the metacarpus, a distal surface portion opposite the base and serving as a contact and friction surface, and a connecting portion connecting the base and the distal surface portion of the head, wherein the distal surface portion of the head is inclined relative to a longitudinal axis of the stem by a predetermined angle other than zero, such that, when the stem is mounted straight in the metacarpus, the distal surface portion of the head can be located in varus, and wherein the base of the head is inclined relative to the longitudinal axis of the stem in the same direction as the distal surface portion, and by an angle equal to said predetermined angle.

2. The implant according to claim 1, wherein the predetermined angle is at least equal to about 10°.

3. The implant according to claim 1, wherein the predetermined angle is equal to about 15°.

4. The implant according to claim 1, wherein the distal surface portion of the head is moreover offset relative to the longitudinal axis of the stem to the side of the implant where the angle between the distal surface portion of the head and the longitudinal axis of the stem is smaller.

5. The implant according to claim 1, wherein the distal surface portion of the head has an axis of symmetry forming the predetermined angle with the longitudinal axis of the stem.

6. The implant according to claim 5, wherein the axis of symmetry of the distal surface portion of the head intersects the longitudinal axis of the stem substantially at the point of intersection between a plane defined by the base of the head and the longitudinal axis of the stem.

7. The implant according to claim 5, wherein the axis of symmetry of the distal surface portion of the head intersects the longitudinal axis of the stem at a point located between a distal end of the stem and the point of intersection between a plane defined by the base of the head and the longitudinal axis of the stem.

8. The implant according to claim 1, wherein the base of the head is substantially perpendicular to the longitudinal axis of the stem.

9. The implant according to claim 1, consisting of a trapezometacarpal implant.

10. The implant according to claim 9, wherein the distal surface portion of the head has a convex shape.

11. The implant according to claim 10, wherein the ratio between a radius of curvature of the distal surface portion of the head and the length of the stem, measured along the longitudinal axis of the stem between a distal end of the stem and the point of intersection between a plane defined by the base of the head and the longitudinal axis of the stem, is at least equal to 0.6.

12. The implant according to claim 9, wherein the ratio between the diameter of the head, measured along a longitudinal axis of the head inclined relative to the longitudinal axis of the stem in the same direction as the distal surface portion and by an angle equal to said predetermined angle, and the length of the stem, measured along the longitudinal axis of the stem between a distal end of the stem and the point of intersection between a plane defined by the base of the head and the longitudinal axis of the stem, is at least equal to 0.84.

13. The implant according to claim 9, wherein the base of the head is inclined relative to the longitudinal axis of the stem in the same direction as the distal surface portion and by an angle equal to said predetermined angle $\alpha$, and the ratio between the thickness of the head and the length of the stem, measured along the longitudinal axis of the stem between a distal end of the stem and the point of intersection between a plane defined by the base of the head and the longitudinal axis of the stem, is at most equal to 0.42.

14. The implant according to claim 1, wherein at least the distal surface portion of the head is of pyrocarbon.

15. The implant of claim 1, wherein when the implant is implanted in a patient, the distal surface portion of the head is in direct contact with the bone located facing the proximal end of the metacarpus.

* * * * *